United States Patent
Bugeja

(10) Patent No.: US 8,118,030 B1
(45) Date of Patent: Feb. 21, 2012

(54) HEAD POSITION CONTROL DEVICE

(76) Inventor: Edward L. Bugeja, Chesapeake, VA (US)

( * ) Notice: Subject to any disclaimer, the term of this patent is extended or adjusted under 35 U.S.C. 154(b) by 404 days.

(21) Appl. No.: 11/975,941

(22) Filed: Oct. 23, 2007

(51) Int. Cl.
*A61F 5/56* (2006.01)
*A61G 15/00* (2006.01)

(52) U.S. Cl. ........................................ 128/848; 128/845

(58) Field of Classification Search .................. 128/848, 128/845; 2/425; 5/636; 606/204.15
See application file for complete search history.

(56) References Cited

U.S. PATENT DOCUMENTS

| | | |
|---|---|---|
| 132,500 A | 12/1872 | Sullivan |
| 876,491 A | 1/1908 | Rohwen |
| 898,379 A | 9/1908 | Liebhart |
| 2,304,235 A | 12/1942 | Boots |
| 4,528,705 A * | 7/1985 | Greenawalt ........................ 5/644 |
| 4,679,263 A * | 7/1987 | Honer ................................ 5/640 |
| 5,036,865 A | 8/1991 | Keaton |
| 5,081,447 A | 1/1992 | Echols |
| 5,381,801 A | 1/1995 | McShane |
| 5,893,365 A | 4/1999 | Anderson |
| 6,289,893 B1 | 9/2001 | Levitt |
| 6,357,444 B1 | 3/2002 | Parker |
| 6,926,008 B1 | 8/2005 | Levitt |
| 7,428,763 B2 * | 9/2008 | Hightower ........................ 5/636 |
| 2005/0043154 A1 | 2/2005 | Atrizadeh |
| 2008/0092908 A1 * | 4/2008 | Costa ............................ 128/848 |

FOREIGN PATENT DOCUMENTS

| | | |
|---|---|---|
| EP | 906044 B1 | 11/2001 |
| WO | WO97/43926 A1 | 11/1997 |

* cited by examiner

*Primary Examiner* — Patricia Bianco
*Assistant Examiner* — Ophelia Hawthorne

(57) ABSTRACT

The Head Position Control (HPC) device significantly reduces snoring and sleep apnea by preventing the face upward positions of the head when a person lies on the back and sides. It is comprised of a cushion mounted on a band that provides means for supporting the cushion on the head. The HPC device is worn as a headband with the cushion positioned at the back of the head. When lying on the back it causes the head to roll to the extreme right or left and when lying on the sides it tilts the nose and mouth slightly downward. This eliminates the mouth and nose up positions of the head that commonly causes snoring and sleep apnea. The device has an additional benefit. As a result of rolling the head to the extreme right or left it stretches neck muscles.

6 Claims, 2 Drawing Sheets

HEAD POSITION CONTROL DEVICE

CROSS-REFERENCE TO RELATED APPLICATIONS

U.S. Patent Documents

U.S. Pat. No. 132,500 10/1872 Sullivan
U.S. Pat. No. 876,491 1/1908 Rohwer
U.S. Pat. No. 898,379 9/1908 Liebhart
U.S. Pat. No. 2,304,235 12/1942 Boots
U.S. Pat. No. 5,036,865 8/1991 Keaton
U.S. Pat. No. 5,081,447 1/1992 Echols
U.S. Pat. No. 5,381,801 1/1995 McShane et al.
U.S. Pat. No. 5,893,365 4/1999 Anderson
U.S. Pat. No. 6,289,893 9/2001 Levitt
U.S. Pat. No. 6,357,444 3/2002 Parker
U.S. Pat. No. 6,926,008 8/2005 Levitt
U.S. Pat. No. 7,428,763 09/2008 Hightower U.S. Patent Application Publications US2005/0043 1542/2005 Atrizadeh

DESCRIPTION

Background of the Invention

1. Field of Endeavor

This invention relates principally to the field of mechanical sleep aids used to control or limit the range of motion of a sleeping person in order to eliminate or reduce snoring and sleep apnea.

2. Description of Prior Art

It is well known that sleeping in the supine position exacerbates snoring and sleep apnea. Many people who snore have been nudged by their bed partner and instructed to roll over onto their side. Research studies have documented that 60% of patients diagnosed with Obstructive Sleep Apnea (OSA) have position dependent OSA. These patients have a dramatic increase in the frequency of apnea events when sleeping in the supine position, versus the side or prone position. Therefore, many devices to reduce snoring and sleep apnea involve methods or devices to prevent sleeping on one's back.

In addition to the methods discussed above, Controlled Positive Air Pressure (CPAP) machines are used to treat obstructive sleep apnea and snoring by providing controlled positive air pressure to the nostrils in order to open the air way. These machines are the most effective means of treating these conditions and are prescribed after sleep studies are performed to diagnose the severity of obstructive sleep apnea. However, they are expensive, invasive, and many find them uncomfortable. A solution is needed that is inexpensive and non-invasive, controlling only the position of the head to reduce or eliminate snoring and sleep apnea. This inventor's device targets individuals whose condition is not serious enough to warrant an expensive CPAP machine and those individuals who cannot or will not wear a CPAP machine.

SUMMARY

The Head Position Control (HPC) device reduces snoring and sleep apnea by controlling head position. The device discussed herein controls head position in both the supine and side sleeping positions.

The device is comprised of a band with a cushion mounted on the outside of the band. It is worn as a headband. In the supine position it causes the head to roll to the extreme right or left eliminating the mouth and nose up position of the head that commonly causes snoring and sleep apnea. In the side position it tilts the nose and mouth slightly downward allowing the tongue to move forward.

The device has an additional benefit. In the supine position it stretches neck muscles reducing neck soreness due to muscle tightness.

DESCRIPTION OF THE DRAWINGS

These features and advantages will be understood in light of the following drawings of the HPC device.

DETAILED DESCRIPTION OF THE INVENTION

The Head Position Control (HPC) device is designed to significantly reduce snoring and sleep apnea via the control of head position. It is comprised of a pear shaped cushion 1 mounted on a band 2.

Figure 1:
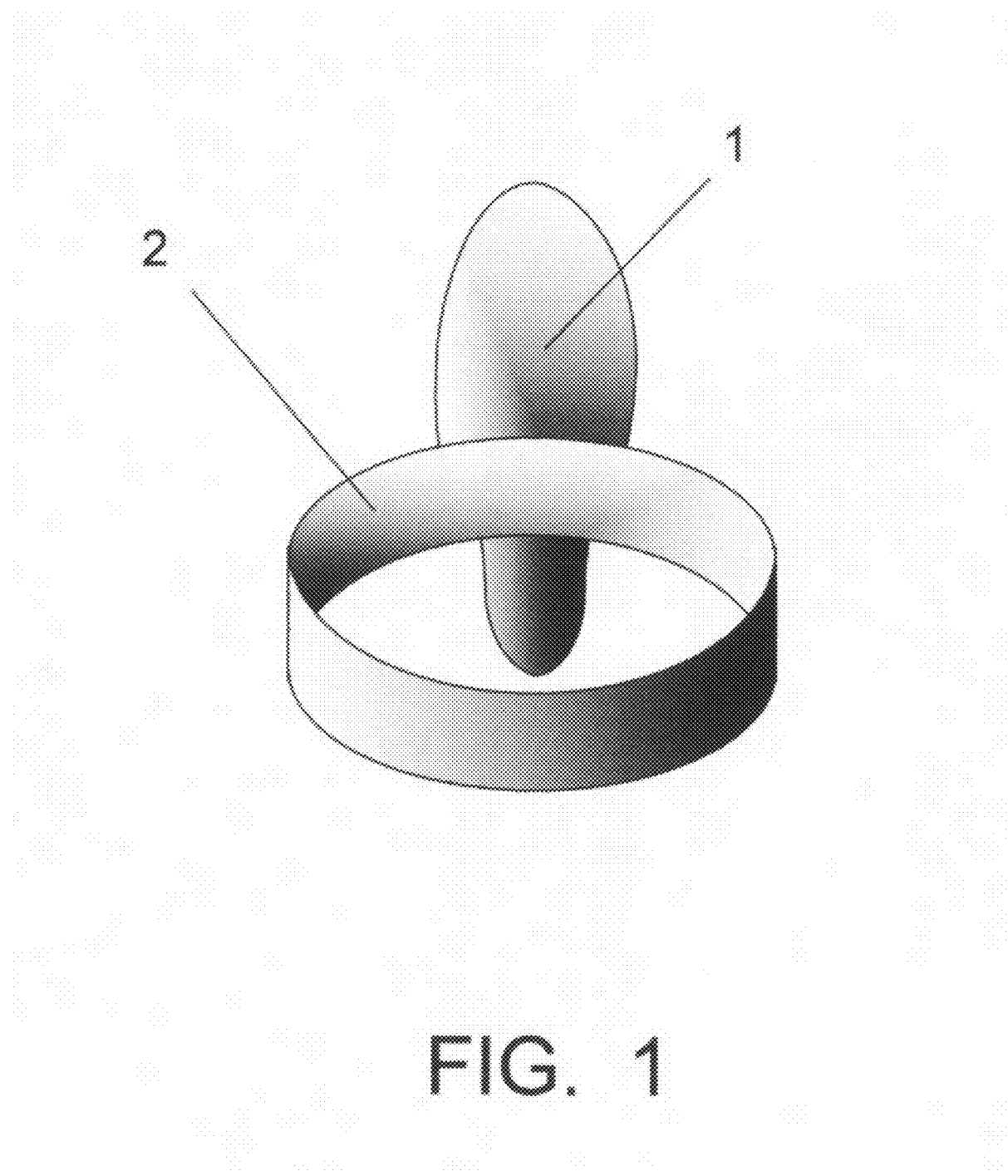
FIG. 1 is a perspective front-view of the HPC device.
Figure 2:
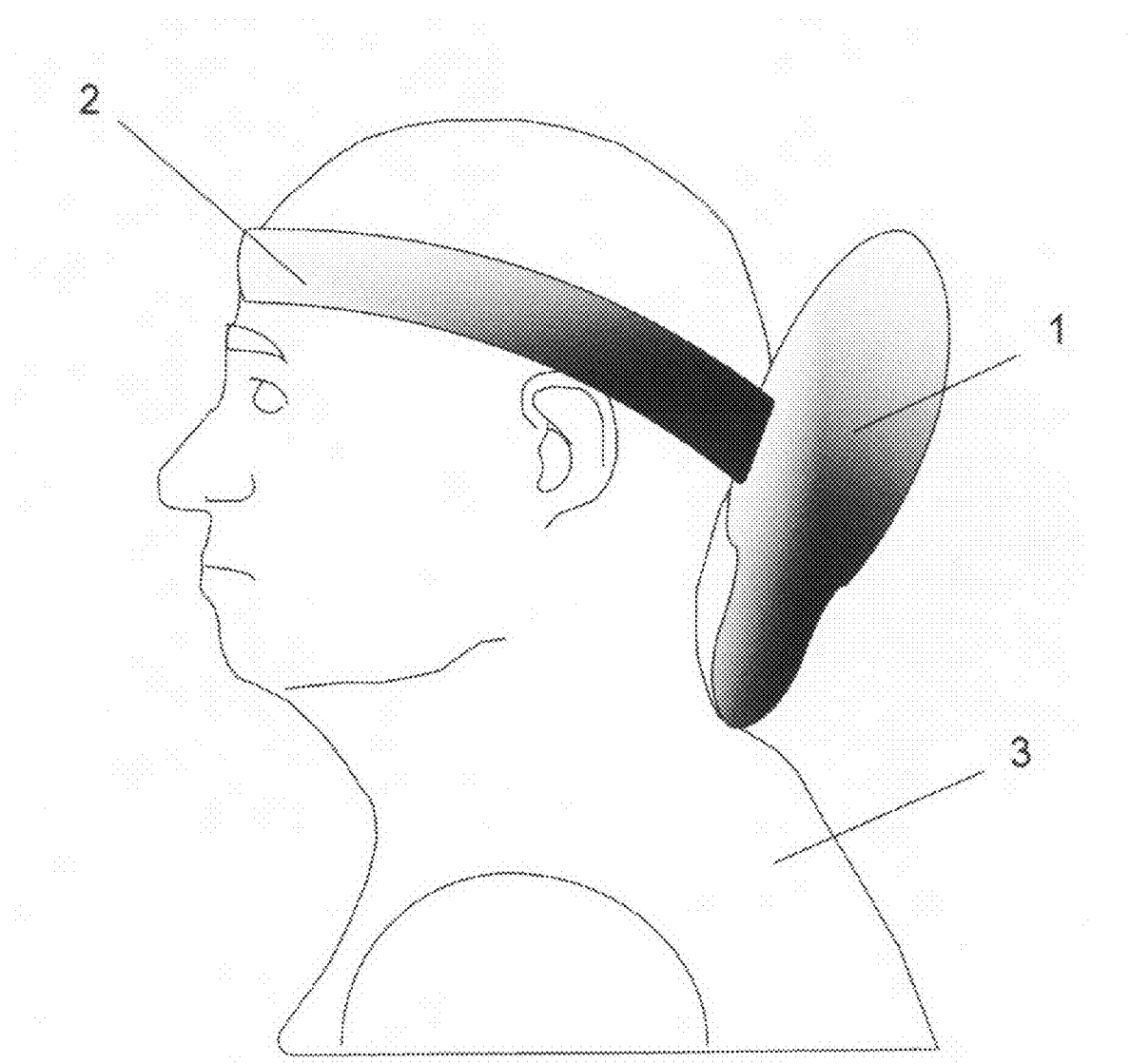
FIG. 2 is side-view of the HPC device that illustrates the HPC device worn by the inventor 3.

The HPC device is shown worn as a headband by the inventor 3 in FIG. 2. The band 2 is placed on the head covering the forehead and resting just above both ears with the cushion 1 at the rear of the head. The shape of cushion 1 is shown as a pear shape in the figures, but is not restricted to this shape. The shape and the size of cushion 1 are determined such that when lying on the back, it causes the head to roll to the extreme right or left and tilts the mouth and nose downward in the side positions. This prevents the face upward positions of the head that results in snoring and sleep apnea in a very large percentage of people. In the supine sleep position with the mouth and nose up, the relaxed tongue and soft palate fall to the back of the throat due to the effects of gravity and restricts the airway. The narrower airway causes the velocity of the air to increase resulting in vibration of the soft tissues known as snoring. When the airway is completely blocked off the result is sleep apnea. The HPC device allows sleeping in all the normal body positions while eliminating the face upward positions of the head. This allows the tongue to fall to the side of the mouth, reducing the deleterious gravity effects when sleeping on the back. When the head is forced to roll to the right or to the left, the neck muscles that are used to turn the head are stretched. If worn regularly, this stretching action will maintain and may even increase the range of motion of the head to either side. It is noted here that the device should not be used if neck damage or disease is present.

While the present invention has been described in terms of the preferred embodiment, other similar embodiments may be used for performing the same function. Therefore, the present invention should be construed in breath and scope in accordance with the recitation of the appended claims.

What is claimed is:

1. A device for preventing a user's face to be in the upward position when the user lies on one's back and sides to reduce snoring and sleep apnea when sleeping, the device consisting of:

(a) a cushion adapted to support the back of a user's head, wherein said cushion causes said user's head to roll to the right or left when lying on their back and tilt the mouth and nose slightly downward in the side positions, said cushion having generally a pear shape having a top portion that is wider than a more narrow lower portion, said cushion is sized to extend along the occipital region of the back of the user's head;

(b) a band for mounting said cushion on and thereby supporting said cushion on the head of the user.

2. The device according to claim 1, wherein said band is composed of soft, comfortable material.

3. The device according to claim 1, wherein said cushion is composed of a resilient material.

4. A method for preventing a user's face to be in the upward position when the user lies on one's back and sides to reduce snoring and sleep apnea when sleeping, the method consisting of:

(a) providing a cushion adapted to support the back of a user's head, wherein said cushion causes said user's head to roll to the right or left when lying on their back and tilt the mouth and nose slightly downward in the side positions, said cushion having generally a pear shape having a top portion that is wider than a more narrow lower portion, said cushion is sized to extend along the occipital region of the back of the user's head;

(b) providing a band for mounting said cushion on and thereby supporting said cushion on the head of the user.

5. The method according to claim 4, wherein said band is composed of soft, comfortable material.

6. The method according to claim 4, wherein said cushion is composed of a resilient material.

* * * * *